(12) United States Patent
Diaz Quijano et al.

(10) Patent No.: US 11,041,074 B2
(45) Date of Patent: Jun. 22, 2021

(54) METHOD FOR THE PRODUCTION OF GRANULES COMPRISING SURFACE-REACTED CALCIUM CARBONATE

(71) Applicant: Omya International AG, Oftringen (CH)

(72) Inventors: Carolina Diaz Quijano, Oftringen (CH); Daniel E. Gerard, Basel (CH); Joachim Schoelkopf, Oberkulm (CH); Patrick A. C. Gane, Rothrist (CH)

(73) Assignee: Omya International AG, Oftringen (CH)

( * ) Notice: Subject to any disclaimer, the term of this patent is extended or adjusted under 35 U.S.C. 154(b) by 438 days.

(21) Appl. No.: 15/774,914

(22) PCT Filed: Dec. 1, 2016

(86) PCT No.: PCT/EP2016/079500
§ 371 (c)(1),
(2) Date: May 9, 2018

(87) PCT Pub. No.: WO2017/093437
PCT Pub. Date: Jun. 8, 2017

(65) Prior Publication Data
US 2018/0327604 A1  Nov. 15, 2018

(30) Foreign Application Priority Data

Dec. 1, 2015 (EP) .................................... 15197395

(51) Int. Cl.
*C09C 1/02* (2006.01)
*A61K 9/16* (2006.01)
*C01F 11/18* (2006.01)

(52) U.S. Cl.
CPC ............ *C09C 1/021* (2013.01); *A61K 9/1617* (2013.01); *C01F 11/183* (2013.01);
(Continued)

(58) Field of Classification Search
CPC .. C09C 1/021; C01P 2004/03; C01P 2004/61; C01P 2004/62; C01P 2006/10;
(Continued)

(56) References Cited

U.S. PATENT DOCUMENTS 3,661,610 A * 5/1972 Ferris .................. C09C 1/42
106/462
4,985,459 A  1/1991 Sunshine et al.
(Continued)

FOREIGN PATENT DOCUMENTS

EP  1974807 B1  3/2010
EP  2168572 A1  3/2010
(Continued)

OTHER PUBLICATIONS

International Search Report dated Jan. 19, 2017 from PCT/EP2016/079500.
(Continued)

*Primary Examiner* — Pegah Parvini
*Assistant Examiner* — Ross J Christie
(74) *Attorney, Agent, or Firm* — Schwegman Lundberg & Woessner, P. A.

(57) ABSTRACT

The present invention relates to a method for the production of granules comprising surface-reacted calcium carbonate, as well as to the granules obtained thereby and their use.

21 Claims, 2 Drawing Sheets

(52) U.S. Cl.
CPC ........ *C01F 11/185* (2013.01); *C01P 2004/03* (2013.01); *C01P 2004/61* (2013.01); *C01P 2004/62* (2013.01); *C01P 2006/10* (2013.01); *C01P 2006/12* (2013.01); *C01P 2006/14* (2013.01)

(58) Field of Classification Search
CPC ............. C01P 2006/12; C01P 2006/14; A61K 9/1617; C01F 11/183; C01F 11/185
See application file for complete search history.

(56) References Cited

U.S. PATENT DOCUMENTS

| | | | |
|---|---|---|---|
| 6,666,953 B1 * | 12/2003 | Gane | ................... D21H 17/675 106/464 |
| 2003/0099741 A1 | 5/2003 | Gubler | |
| 2003/0157213 A1 | 8/2003 | Jenkins | |
| 2003/0206993 A1 | 11/2003 | Gubler | |
| 2004/0020410 A1 * | 2/2004 | Gane | ....................... C09C 1/021 106/464 |
| 2013/0108872 A1 * | 5/2013 | Magome | ................ A61K 47/38 106/203.3 |

FOREIGN PATENT DOCUMENTS

| | | |
|---|---|---|
| EP | 2264108 A1 | 12/2010 |
| EP | 2264109 A1 | 12/2010 |
| EP | 1974806 B1 | 9/2011 |
| EP | 1982759 B1 | 9/2011 |
| EP | 1975310 B1 | 12/2011 |
| EP | 2589430 A1 | 5/2013 |
| EP | 2662416 A1 | 11/2013 |
| EP | 2719373 A1 | 4/2014 |
| EP | 2719376 A1 | 4/2014 |
| EP | 2921173 A1 | 9/2015 |
| FR | 2787802 B1 | 2/2001 |
| TW | 201536336 A | 10/2015 |
| WO | 0039222 A1 | 7/2000 |
| WO | 2004083316 A1 | 9/2004 |
| WO | 2005121257 A2 | 12/2005 |
| WO | 2009074492 A1 | 6/2009 |
| WO | 2010037753 A1 | 4/2010 |
| WO | 2010146530 A1 | 12/2010 |
| WO | 2010146531 A1 | 12/2010 |

OTHER PUBLICATIONS

Written Opinion of the International Searching Authority dated Jan. 19, 2017 from PCT/EP2016/079500.

* cited by examiner

METHOD FOR THE PRODUCTION OF GRANULES COMPRISING SURFACE-REACTED CALCIUM CARBONATE

CROSS-REFERENCE TO RELATED APPLICATIONS

This is a U.S. national phase of PCT Application No. PCT/EP2016/079500, filed Dec. 1, 2016, which claims priority to European Application No. 15197395.5, filed Dec. 1, 2015.

The present invention relates to a method for the production of granules comprising surface-reacted calcium carbonate, as well as to the granules obtained thereby and their use.

In the year of 1998, a new type of surface-reacted calcium carbonate was first described in FR 2787802 B1, subsequently in WO 00/39222 A1 and US 2004/0020410 A1, and is based on the reaction of natural ground calcium carbonate with gaseous $CO_2$ and with one or more medium-strong to strong $H_3O^+$ ion providers. The obtained product is a porous calcium carbonate having a special surface structure, porosity, and specific surface area providing a reduction in the weight of paper for a constant surface area without loss of physical properties, when it is used as a pigment or coating filler for the said paper.

In WO 2004/083316 A1, a further advantageous modification in the preparation of this surface-reacted calcium carbonate is described, wherein aluminium silicate, synthetic silica, calcium silicate, silicates and/or monovalent salt are involved, and which are also useful in paper-making applications.

Also, WO 2005/121257 A2 refers to the addition of advantageous additives in the production of said surface-reacted calcium carbonate, wherein one or more compounds of formula R—X are added, which, e.g. are selected from fatty acids, fatty amines or fatty alcohols.

WO 2009/074492 A1 especially relates to the optimization of the known process as regards precipitated calcium carbonate, as it turned out that due to the special conditions in the precipitation of calcium carbonate, the process useful for natural ground calcium carbonate did not provide the same good results for the surface-reaction of synthetic precipitated calcium carbonate.

Several further optimizations and modifications of the process for the preparation of surface-reacted calcium carbonate followed such as those described in EP 2 264 108 A1 (WO 2010/146530 A1) and EP 2 264 109 A1 (WO 2010/146531 A1) involving the use of weak acids in the preparation of surface-reacted calcium carbonate.

However, none of these documents explicitly mentions granulation of surface-reacted calcium carbonate.

Granules, however, in many applications are of considerable importance and more preferred than powders. Thus, agglomeration of powders leading to granules typically having a size range between 0.2 to 4.0 mm depending on their subsequent use is widely used to improve physical properties of powders like: wettability, flowability, bulk density and product appearance.

Furthermore, granulation is carried out, e.g. to prevent the segregation of the constituents of powder mixes, to prevent dusting or to improve flowability.

Granulation, i.e. the process in which the primary powder particles are made to adhere to form larger, multiparticle entities is a process of collecting particles together by creating bonds between them e.g. by a binding agent.

One of the most important types of granulation is wet granulation, wherein granules are formed by the addition of a granulation liquid onto a powder bed which is under the influence of an impeller. The agitation resulting in the system along with the wetting of the components within the formulation results in the agglomeration of the primary powder particles to produce wet granules. The granulation liquid contains a solvent which must be volatile so that it can be removed by drying, and be non-toxic. Water mixed into the powders can form bonds between powder particles that are strong enough to lock them together. However, once the water dries, the powders may fall apart. Therefore, water may not be strong enough to create and hold a bond. In such instances, the granulation liquid includes a binder.

Regarding surface-reacted calcium carbonate, also granules are generally known. For example, in EP 2 264 108 A1 (WO 2010/146530 A1), it is mentioned that the surface-reacted calcium carbonate obtained from the process described therein may be in the form of a cake, granules or a powder, and also in several documents describing different uses of surface-reacted calcium carbonate, such as in water purification, as a controlled release carrier, in fast disintegrating dosage forms, or gastroretentive drug formulation and delivery systems (EP 1975 310 B1, EP 1982 759 B1, EP 11974 807 B1, EP 1974 806 B1, EP 2 589 430 A1, WO 2010/037753 A1, EP 2 719 373 A1, or EP 2 719 376A1), granules are generally mentioned.

These granules, however, which are either obtained as a result of the basic process of producing surface-reacted calcium carbonate, or by wet granulation, suffer from several disadvantages, such as e.g. a low stability and high fragility, or need a high amount of binder in order to increase stability of the granules.

Thus, surface-reacted calcium carbonate can be granulated using various methods, but, due to its porosity, conventional processes do not provide the desired result. Granulation has proven to be very difficult to process a stable product, requiring a large amount of binder and still failing to show much strength.

In this regard, unpublished EP applications 14 170 578.0 and EP 14 173 325.3 refer to a method for the production of granules comprising surface-reacted calcium carbonate, where it was found that, if the pores of the porous structure of the surface-reacted calcium carbonate particles are first saturated with the granulation liquid, whereas the binder is added afterwards, not only the stability of the resulting granules may be increased, but also the amount of binder may be decreased.

However, none of these documents mentions granulation of surface-reacted calcium carbonate which are loaded with an active ingredient.

Thus, it is the object of the present invention to provide a method for the production of granules comprising surface-reacted calcium carbonate being loaded with an active ingredient. It is a further object of the present invention to provide a method for the production of granules comprising surface-reacted calcium carbonate having a reduced binder demand, wherein the granules have an improved stability.

The foregoing and other objectives are solved by the subject-matter as defined herein in claim 1.

Advantageous embodiments of the inventive method for the production of granules comprising surface-reacted calcium carbonate are defined in the corresponding sub-claims.

According to one aspect of the present application a method for the production of granules comprising surface-reacted calcium carbonate is provided. The method is characterized by the steps of a) providing surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
b) providing one or more active ingredient(s) in liquid form,
c) saturating the surface-reacted calcium carbonate with the one or more active ingredient(s) in liquid form,
d) providing one or more binder, and
e) combining the saturated surface-reacted calcium carbonate obtained in step c) with the one or more binder of step d) under agitation in an agitation device.

The inventors surprisingly found out that the foregoing method for the production of granules comprising surface-reacted calcium carbonate according to the present invention has a reduced binder demand and provides granules which are loaded with an active ingredient and further have an improved stability.

It should be understood that for the purposes of the present invention, the following terms have the following meanings:

Where the term "comprising" is used in the present description and claims, it does not exclude other non-specified elements of major or minor functional importance. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

According to another aspect of the present invention, granules comprising surface-reacted calcium carbonate obtained by the method, as defined herein, are provided.

According to a further aspect of the present invention, the use of the granules comprising surface-reacted calcium carbonate, as defined herein, as fragrance delivery system, flavour delivery system, nutraceutical delivery system, pesticide delivery system, preservation delivery system, antioxidant delivery system, crop protection delivery system, fertilization delivery system, a catalytic system, a shielding system for delicate molecules, a carrier system, a chemical delivery system or pharmaceutical delivery system is provided. Preferably, the granules comprising surface-reacted calcium carbonate, as defined herein, are used in form of a tablet, mini-tablet, capsule or pellet.

According to one embodiment of the present invention, the natural ground calcium carbonate is selected from calcium carbonate containing minerals selected from the group comprising marble, chalk, dolomite, limestone and mixtures thereof; and that the precipitated calcium carbonate is selected from the group comprising precipitated calcium carbonates having aragonitic, vateritic or calcitic mineralogical crystal forms or mixtures thereof.

According to another embodiment of the present invention, the surface-reacted calcium carbonate has i) a specific surface area of from 15 $m^2/g$ to 200 $m^2/g$, preferably from 27 $m^2/g$ to 180 $m^2/g$, more preferably from 30 $m^2/g$ to 160 $m^2/g$, even more preferably from 45 $m^2/g$ to 150 $m^2/g$, and most preferably from 48 $m^2/g$ to 140 $m^2/g$, measured using nitrogen and the BET method according to ISO 9277, and/or ii) a volume median grain diameter $d_{50}$ of from 1 to 75 µm, preferably from 2 to 50 µm, more preferably 3 to 40 µm, even more preferably from 4 to 30 µm, and most preferably from 5 to 15 µm, and/or iii) an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 $cm^3/g$, calculated from mercury porosimetry measurement, and/or iv) a grain diameter $d_{98}$ (vol) of from 2 to 150 µm, preferably from 4 to 100 µm, more preferably 6 to 80 µm, even more preferably from 8 to 60 µm, and most preferably from 10 to 30 µm.

According to yet another embodiment of the present invention, in step b), the one or more active ingredient(s) is/are dissolved in a solvent, preferably the solvent is selected from the group comprising water, methanol, ethanol, n-butanol, isopropanol, n-propanol, acetone, dimethylsulphoxide, dimethylformamide, tetrahydrofurane, vegetable oils and the derivatives thereof, animal oils and the derivatives thereof, molten fats and waxes, and mixtures thereof, and more preferably the solvent is water, ethanol and/or acetone.

According to one embodiment of the present invention, in step b), the one or more active ingredient(s) is/are selected from the group comprising fragrances, flavors, herbal extracts, fruit extracts, nutrients, trace minerals, repellents, food, cosmetics, sweeteners, flame retardants, enzymes, pesticides, fertilizers, preserving agents, antioxidants, reactive chemicals, pharmaceutically active agents or pharmaceutically inactive precursors thereof, and mixtures thereof.

According to another embodiment of the present invention, the one or more binder of step d) is selected from the group comprising synthetic polymers such as methylcellulose, ethylcellulose, sodium carboxymethylcellulose, hydroxypropyl methylcellulose (HPMC), hydroxypropylcellulose (HPC), ethylhydroxyethylcellulose (EHEC), polyvinyl pyrrolidone (PVP), polyethylene glycol (PEG), polyvinyl alcohols, polymethacrylates; and natural binders such as plant gums, e.g. acacia, tragacanth, sandarac, ghatti, karaya, locust bean and guar, proteins such as gelatin, casein, collagen; saccharides and polysaccharides such as starch and its derivatives, inulin, cellulose, pectins, carrageenans and sugars; animal exudates such as shellac; beeswax, alginic acid, and mixtures thereof.

According to yet another embodiment of the present invention, the one or more binder of step d) is added in an amount of from 0.1 to 50 wt.-%, preferably of from 0.2 to 25 wt.-%, more preferably of from 0.3 to 20 wt.-%, even more preferably of from 0.4 to 15 wt.-%, most preferably of from 0.5 to 10 wt.-%, e.g. 1 wt.-%, based on the total dry weight of surface-reacted calcium carbonate of step a).

According to one embodiment of the present invention, in step e), the agitation device is selected from the group comprising Eirich mixers, fluidized bed dryers/granulators, plate granulators, table granulators, drum granulators, disc granulators, dish granulators, ploughshare mixer, vertical or horizontal mixers, high or low shear mixer, high speed blenders and rapid mixer granulators.

According to another embodiment of the present invention, in step e), the one or more binder is added to the agitation device simultaneously with or after the saturated surface-reacted calcium carbonate obtained in step c).

According to yet another embodiment of the present invention, the method further comprises a step f) of adding further surface-reacted calcium carbonate or saturated surface-reacted calcium carbonate or mixtures thereof, and/or solvent, preferably water, to the mixture obtained in step e) until an agglomeration of the particles is observed.

According to one embodiment of the present invention, further surface-reacted calcium carbonate or saturated surface-reacted calcium carbonate or mixtures thereof is added in an amount of from 1 to 30 wt.-%, preferably of from 5 to 25 wt.-%, more preferably of from 8 to 20 wt.-%, based on the total dry weight of the surface-reacted calcium carbonate provided in step a).

According to another embodiment of the present invention, the method further comprises a step g) of removing the solvent from the mixture obtained in step c) and/or e) and/or f).

According to yet another embodiment of the present invention, in step g), the solvent is removed by means of separating the solvent from the resulting granules, preferably by drying by means selected from the group comprising drying in a rotational oven, jet-drying, fluidized bed drying, freeze drying, flash drying and temperature-controlled high or low shear mixer.

According to one embodiment of the present invention, the granules comprising surface-reacted calcium carbonate obtained after step e) and/or f) and/or g) have a volume median particle size of from 0.1 to 6 mm, preferably 0.2 to 5 mm, more preferably from 0.2 to 4 mm, especially preferably from 0.2 to 0.6 mm or 0.6 mm to 2 mm, determined by sieve fractioning.

According to another embodiment of the present invention, the granules comprising surface-reacted calcium carbonate obtained after step e) and/or f) and/or g) have a specific surface area of from 10 to 180 m$^2$/g, preferably of from 15 to 150 m$^2$/g, more preferably of from 20 to 110 m$^2$/g, most preferably of from 30 to 70 m$^2$/g, measured using nitrogen and the BET method according to ISO 9277.

The inventive method for the production of granules comprising surface-reacted calcium carbonate provides several advantages. Firstly, the inventive method provides granules which are loaded with an active ingredient. Secondly, the inventive method provides granules having an improved stability. In addition thereto, the inventive method has a reduced binder demand.

In the following, details and preferred embodiments of the inventive method will be set out in more details. It is to be understood that these technical details and embodiments also apply to the inventive products as well as to their use.

Method Step a)

In step a) of the method of the present invention, surface-reacted calcium carbonate is provided.

The surface-reacted calcium carbonate is a reaction product of natural ground calcium carbonate or precipitated calcium carbonate with carbon dioxide and one or more $H_3O^+$ ion donors, wherein the carbon dioxide is formed in-situ by the $H_3O^+$ ion donors treatment and/or is supplied from an external source.

A $H_3O^+$ ion donor in the context of the present invention is a Brønsted acid and/or an acid salt.

In a preferred embodiment of the invention the surface-reacted calcium carbonate is obtained by a process comprising the steps of: (a) providing a suspension of natural or precipitated calcium carbonate, (b) adding at least one acid having a p$K_a$ value of 0 or less at 20° C. or having a p$K_a$ value from 0 to 2.5 at 20° C. to the suspension of step a), and (c) treating the suspension of step (a) with carbon dioxide before, during or after step (b). According to another embodiment the surface-reacted calcium carbonate is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a p$K_a$ of greater than 2.5 and les than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a p$K_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural or precipitated calcium carbonate is in form of particles having a weight median particle size $d_{50}$ of 0.05 to 10.0 μm, preferably 0.2 to 5.0 μm, more preferably 0.4 to 3.0 μm, most preferably 0.6 to 1.2 μm, especially 0.71 μm. According to a further embodiment of the present invention, the natural or precipitated calcium carbonate is in form of particles having a top cut particle size $d_{98}$ of 0.15 to 55 μm, preferably 1 to 40 μm, more preferably 2 to 25 μm, most preferably 3 to 15 μm, especially 4 μm.

The natural and/or precipitated calcium carbonate may be used dry or suspended in water. Preferably, a corresponding slurry has a content of natural or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of surface reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acidic salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acidic salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acidic salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one HO ion donor is selected from the group consisting of hydrochloric acid, sulphuric acid, sulphurous acid, phosphoric acid, oxalic acid, $H_2PO_4^-$ being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural or precipitated calcium carbonate is treated with carbon dioxide. If a strong acid such as sulphuric acid or hydrochloric acid is used for the $H_3O^+$ ion donor treatment of the natural or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in-situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_2O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate is obtained. As can be taken in detail from WO 2009/074492 A1, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in-situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the surface-reacted natural or precipitated calcium carbonate, the natural or precipitated calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural or precipitated calcium carbonate before adding the acid and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with an acid and carbon dioxide has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural or precipitated calcium carbonate in the form of granules or a powder.

The surface reacted calcium carbonate may have different particle shapes, such as e.g. the shape of roses, golf balls and/or brains.

In a preferred embodiment, the surface-reacted calcium carbonate has a specific surface area of from 15 m$^2$/g to 200 m$^2$/g, preferably from 27 m$^2$/g to 180 m$^2$/g, more preferably from 30 m$^2$/g to 160 m$^2$/g, even more preferably from 45 m$^2$/g to 150 m$^2$/g, most preferably from 48 m$^2$/g to 140 m$^2$/g, measured using nitrogen and the BET method. For example, the surface-reacted calcium carbonate has a specific surface area of from 75 m$^2$/g to 100 m$^2$/g, measured using nitrogen and the BET method. The BET specific surface area in the meaning of the present invention is defined as the surface area of the particles divided by the mass of the particles. As used therein the specific surface area is measured by adsorption using the BET isotherm (ISO 9277:1995) and is specified in m$^2$/g.

It is furthermore preferred that the surface-reacted calcium carbonate particles have a volume median grain diameter $d_{50}$ (vol) of from 1 to 75 μm, preferably from 2 to 50 μm, more preferably 3 to 40 μm, even more preferably from 4 to 30 μm, and most preferably from 5 to 15 μm.

It may furthermore be preferred that the surface-reacted calcium carbonate particles have a grain diameter $d_{98}$ (vol) of from 2 to 150 μm, preferably from 4 to 100 μm, more preferably 6 to 80 μm, even more preferably from 8 to 60 μm, and most preferably from 10 to 30 μm.

The value $d_x$ represents the diameter relative to which x % of the particles have diameters less than $d_x$. This means that the $d_{98}$ value is the particle size at which 98% of all particles are smaller. The ds value is also designated as "top cut". The $d_x$ values may be given in volume or weight percent. The $d_{50}$ (wt) value is thus the weight median particle size, i.e. 50 wt.-% of all grains are smaller than this particle size, and the $d_{50}$ (vol) value is the volume median particle size, i.e. 50 vol. % of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 µm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 µm down to about 1-4 µm showing the coarse packing of the sample between any agglomerate structures contributing strongly. Below these diameters lies the fine interparticle packing of the particles themselves. If they also have intraparticle pores, then this region appears bi modal, and by taking the specific pore volume intruded by mercury into pores finer than the modal turning point, i.e. finer than the bi-modal point of inflection, we thus define the specific intraparticle pore volume. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the surface-reacted calcium carbonate has an intra-particle intruded specific pore volume in the range from 0.1 to 2.3 $cm^3/g$, more preferably from 0.2 to 2.0 $cm^3/g$, especially preferably from 0.4 to 1.8 $cm^3/g$ and most preferably from 0.6 to 1.6 cm/g, calculated from mercury porosimetry measurement.

The intra-particle pore size of the surface-reacted calcium carbonate preferably is in a range of from 0.004 to 1.6 µm, more preferably in a range of between 0.005 to 1.3 µm, especially preferably from 0.006 to 1.15 µm and most preferably of 0.007 to 1.0 µm, e.g. 0.004 to 0.51 µm determined by mercury porosimetry measurement.

Method Step b)

In step b) of the method of the present invention, one or more active ingredient(s) in liquid form is/are provided.

In one embodiment of the present invention, the one or more active ingredient(s) comprise(s), preferably consist(s) of, one active ingredient. Alternatively, the one or more active ingredient(s) comprise(s), preferably consist(s) of, two or more active ingredients. For example, the one or more active ingredient(s) comprise(s), preferably consist(s) of, two or three active ingredients.

Preferably, the one or more active ingredient(s) comprise(s), preferably consist(s) of, one active ingredient.

It is one requirement of the present invention that the one or more active ingredient(s) are provided in liquid form.

The term "liquid" in the meaning of the present invention refers to a non-gaseous fluid composition, comprising or consisting of the one or more active ingredient(s), which is readily flowable at the pressure conditions and temperature of use, i.e. the pressure and temperature at which the method, preferably method step c), is carried out.

Thus, it is appreciated that the one or more active ingredient(s) can be liquid in a temperature range from 5 to 200° C., preferably from 10 to 120° C. and most preferably from 10 to 100° C. For example, the one or more active ingredient(s) can be liquid in a temperature range from 5 to 200° C., preferably from 10 to 120° C. and most preferably from 10 to 100° C. at ambient pressure conditions, i.e. at atmospheric pressure. Alternatively, the one or more active ingredient(s) can be liquid in a temperature range from 5 to 200° C., preferably from 10 to 120° C. and most preferably from 10 to 100° C. at reduced pressure conditions, e.g. a pressure of from 100 to 700 mbar.

In one embodiment, the one or more active ingredient(s) is/are liquid at ambient temperature and pressure conditions, e.g., at room temperature, such as from about 5 to 35° C., preferably from 10 to 30° C. and most preferably from 15 to 25° C., and at atmospheric pressure.

Alternatively, the one or more active ingredient(s) is/are molten at the temperature of use, e.g. from about 35 to 200° C., preferably from 45 to 120° C. and most preferably from 55 to 100° C., and at ambient pressure conditions, i.e. at atmospheric pressure, or at reduced pressure conditions, e.g. a pressure of from 100 to 700 mbar.

Alternatively, the one or more active ingredient(s) is/are dissolved in a solvent. That is to say, the one or more active ingredient(s) and the solvent form a system in which no discrete solid particles are observed in the solvent and thus form a "solution".

In one embodiment of the present invention, the solvent is selected from the group comprising water, methanol, ethanol, n-butanol, isopropanol, n-propanol, acetone, dimethylsulphoxide, dimethylformamide, tetrahydrofurane, vegetable oils and the derivatives thereof, animal oils and the derivatives thereof, molten fats and waxes, and mixtures thereof. Preferably, the solvent is water, ethanol and/or acetone. More preferably, the solvent is water.

The term "active ingredient" in the meaning of the present invention refers to a substance having a specific effect in an organism and causing a specific reaction in humans, animals, microorganisms and/or plants.

It is appreciated that the one or more active ingredient(s) may be a chiral compound. Thus, the one or more active ingredient(s) encompass the (R)-enantiomer, (S)-enantiomer and mixtures thereof, e.g. the racemic mixture.

Additionally or alternatively, the one or more active ingredient(s) may be an isomeric compound. Thus, the one or more active ingredient(s) encompass the (Z)-isomer, (E)-isomer and mixtures thereof. For example, if it is stated that the active ingredient is cinnamaldehyde, the cinnamaldehyde may be present as (Z)-cinnamaldehyde and/or (E)-cinnamaldehyde.

For example, the one or more active ingredient(s) is/are selected from the group comprising fragrances, flavours, essential oils, herbal extracts, fruit extracts, nutrients, trace minerals, repellents, food, cosmetics, sweeteners, flame retardants, enzymes, pesticides, fertilizers, preserving agents, antioxidants, reactive chemicals, pharmaceutically active agents or pharmaceutically inactive precursors thereof, and mixtures thereof.

Fragrances are preferably alcohols, aldehydes and/or ketones having a molecular weight of at least about 100 g/mol and which are useful in imparting an odour, fragrance, essence, or scent either alone or in combination with other fragrances. For example, the fragrance can be selected from the group comprising 2,4-dimethyl-3-cyclohexene-1-methanol (floralol), 2,4-dimethyl cyclohexane methanol (dihydro floralol), 5,6-dimethyl-1-methylethenylbicyclo[2.2.1]hept-5-ene-2-methanol (arbozol), α,α,-4-trimethyl-3-cyclohexen-1-methanol (α-terpineol), 2,4,6-trimethyl-3-cyclohexene-1-methanol (isocyclo geraniol), 4-(1-methylethyl)cyclohexane methanol (mayol), α-3,3-trimethyl-2-norborane methanol, 1,1-dimethyl-1-(4-methylcycohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3-dimethyl-Δ²-β-norbornane ethanol (patchomint), 2-methyl-2-cyclohexylethanol, 1-(4-isopropylcyclohexyl)-ethanol, 1-phenylethanol, 1,1-dimethyl-2-phenylethanol, 1,1-dimethyl-2-(4-methyl-phenyl)ethanol, 1-phenylpropanol, 3-phenylpropanol, 2-phenylpropanol (Hydrotropic Alcohol), 2-(cyclododecyl)propan-1-ol (Hydroxy-ambran), 2,2-dimethyl-3-(3-methylphenyl)-propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl-4-(2,2,3-trimethyl-cyclopent-3-enyl)-2-buten-1-ol, 3-methyl-2-buten-1-ol (prenol), 2-methyl-4-(2,2,3-trimethyl-3-cyclopenten-1-yl)-2-buten-1-ol, ethyl 3-hydroxybutyrate, 4-phenyl-3-buten-2-ol, 2-methyl-4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl-4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0.sup.(2,6)]hept-3-yl)-2-penten-1-ol (santalol), 4-methyl-1-phenyl-2-pentanol, 5-(2,2,3-trimethyl-3-cyclopentenyl)-3-methylpentan-2-ol (sandalore), (1-methyl-bicyclo[2.1.1]hepten-2-yl)-2-methylpent-1-en-3-ol, 3-methyl-1-phenylpentan-3-ol, 1,2-dimethyl-3-(1-methylethenyl)cyclopentan-1-ol, 2-isopropyl-5-methyl-2-hexenol, cis-3-hexen-1-ol, trans-2-hexen-1-ol, 2-isoproenyl-4-methyl-4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopopenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclohexanol 2-tert-butylcyclohexanol, 2-tert-butyl-4-methylcyclohexanol (rootanol), 4-isopropyl-cyclohexanol, 4-methyl-1-(I-methylethyl)-3-cyclohexen-1-ol, 2-(5,6,6-trimethyl-2-norbornyl)cyclohexanol, isobornylcyclohexano, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl)cyclohexan-1-ol, heptanol, 2,4-dimethylheptan-1-ol, 6-heptyl-5-hepten-2-ol (isolinalool), 2,4-dimethyl-2,6-heptandienol 6,6-dimethyl-2-oxymethyl-bicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-trimethylbicyclo[2.2.1]heptan-2-ol, 26-dimethylheptan-2-ol (dimetol), 2,6,6-trimethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6-octadien-1-ol (nerol) 3,7-dimethyl-7-methoxyoctan-2-ol (osyrol) 3,7-dimethyl-1,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl-4-vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3, 7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6-nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl-1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl-1,6,10,-dodecatrien-3-ol (nerolidol), 3,7,11,15-tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy-4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy-1-methylbenzene, 2-tert-butyl-4-methyl-1-hydroxybenzene, 1-ethoxy-2-hydroxy-4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbornanol (fenchol), 3a,4,5,6,7,7a-hexahydro-2,4-dimethyl-4,7-methano-1H-inden-5-ol, 3a,4,5,6,7,7a-hexahydro-3,4-dimethyl-4,7-methano-1H-inden-5-ol, 2-methyl-2-vinyl-5-(1-hydroxy-1-methylethyl)tetra-hydrofuran, p-caryophyllene alcohol, vanillin, ethyl vanillin, cinnamaldehyde, benzaldehyde, phenyl acetaldehyde, heptylaldehyde, octylaldehyde, decylaldehyde, undecylaldehyde, undecylenic aldehyde, dodecylaldehyde, tridecylaldehyde, methylnonyl aldehyde, didecylaldehyde, anisaldehyde, citronellal, citronellyloxyaldehyde, cyclamen aldehyde, α-hexyl cinnamaldehyde, hydroxycitronellal, α-methyl cinnamaldehyde, methylnonyl acetaldehyde, propylphenyl aldehyde, citral, perilla aldehyde, tolylaldehyde, tolylacetaldehyde, cuminaldehyde, LILIAL®, salicyl aldehyde, α-amylcinnamaldehyde and heliotropin and mixtures thereof.

Various essential oils, herbal extracts and/or fruit extracts may also be used, preferably those with various medicinal or dietary supplement properties. Essential oils, herbal extracts and/or fruit extracts are generally extracts or aromatic plants, plant parts, fruit or fruit parts that can be used medicinally or for flavouring. Suitable herbal extracts and/or fruit extracts can be used singly or in various mixtures. Commonly used essential oils, herbal extracts and/or fruit extracts include Echinacea, Goldenseal, Calendula, Rosemary, Thyme, Kava Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, Ginger, eugenol-containing oils and combinations thereof.

A variety of nutrients may be used including virtually any vitamin, mineral and/or phytochemical. For example, vitamin A, vitamin B1, vitamin B6, vitamin B12, vitamin B2, vitamin B6, vitamin D, vitamin E, i.e. tocopheroles, vitamin K, thiamine, riboflavin, biotin, folic acid, niacin, pantothenic acid, Q10, alpha lipoic acid, dihydrolipoic acid, curcumin, xanthophylls, beta cryptoxanthin, lycopene, lutein, zeaxanthin, astaxanthin, beta-carotene, carotenes, mixed carotenoids polyphenols, flavonoids, sodium, potassium, calcium, magnesium, sulphur, chlorine, choline, and/or phytochemicals such as carotenoids, chlorophyll, chlorophyllin, fibre, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof, may be used. Examples of nutrients that can be used as active ingredient(s) are set forth in U.S. Patent Application Publication Nos. 2003/0157213 A1, 2003/0206993 and 2003/0099741 A1 which are incorporated in their entirety herein by reference for all purposes.

In one embodiment, trace minerals can be used, e.g. manganese, zinc, copper, fluorine, molybdenum, iodine, cobalt, chromium, selenium, phosphorous, and combinations thereof.

Enzymes can include but are not limited to coenzyme Q10, pepsin, phytase, trypsin, lipases, proteases, cellulases, lactase and combinations thereof.

Pesticides are preferably any known herbicide, insecticide, insect growth regulator, nematicide, termiticide, molluscicide, piscicide, avicide, rodenticide, predacide, bactericide, insect repellent, animal repellent, antimicrobial, fungicide, disinfectant (antimicrobial), and sanitizer known to the skilled person.

It is to be noted that the preserving agent may be any such compound known to the skilled person. For example, preserving agents may include, but are not limited to, phenoxyethanol, ethylhexylglycerin, parabens such as methyl paraben, ethyl paraben, propyl paraben, butyl paraben and mixtures thereof, benzalkonium chloride, chlorbutanol, benzyl alcohol, cetylpyridinium chloride, tartaric acid, lactic acid, malic acid, acetic acid, benzoic acid, sodium benzoate, sorbic acid, potassium sorbate and mixtures thereof.

Antioxidants are preferably selected from the group comprising butylhydroxyanisol (BHA), butylhydroxytoluol (BHT), gallate, carotinoid, polyphenols such as resveratrol, flavonoid and mixtures thereof, derivatives of polyphenols, tocopherol and salts thereof, betacarotin, ubichinon, tocotrienol, dihydroquercetin, antioxidants of natural origin and mixtures thereof. If the antioxidant is of natural origin, the antioxidant can be e.g. a conifer extract, pinus pinaster bark extract such as Pycnogenol® from Horphag, Switzerland, and/or *Emblica officinalis* fruit extract such as Sabenry® from Sabinsa corporation, Germany.

The pharmaceutically active agent or pharmaceutically inactive precursor thereof is preferably selected from the group comprising pharmaceutically active agent or pharmaceutically inactive precursor of synthetic origin, semi-synthetic origin, natural origin and combinations thereof.

Thus, a pharmaceutically active agent refers to pharmaceutically active agents which are of synthetic origin, semi-synthetic origin, natural origin and combinations thereof. Further, a pharmaceutically inactive precursor of the pharmaceutically active agent refers to pharmaceutically inactive precursors which are of synthetic origin, semi-synthetic origin, natural origin and combinations thereof and will be activated at a later stage to the respective pharmaceutically active agent.

The activation of such pharmaceutically inactive precursor is known to the skilled person and commonly in use, e.g. activation in the stomach and/or gastro-intestinal pathway—such as acidic activation or tryptic- or chimotryptic cleavage.

It lies within the understanding of the skilled person that the mentioned activation methods are of mere illustrative character and are not intended to be of limiting character.

It is to be noted that the pharmaceutically active agent or pharmaceutically inactive precursor thereof, may be any such compound known to the skilled person.

Pharmaceutically active agents thus include any compound that provides prophylactic and/or therapeutic properties when administered to humans and/or animals. Examples include, but are not limited to, pharmaceutical actives, therapeutic actives, veterinarian actives, nutraceuticals, and growth regulators.

The pharmaceutically active agent or pharmaceutically inactive precursor thereof can be an anti-inflammatory agent. Such agents may include, but are not limited to, non-steroidal anti-inflammatory agents or NSAIDs, such as propionic acid derivatives; acetic acid derivatives; fenamic acid derivatives; biphenylcarboxylic acid derivatives; and oxicams. All of these NSAIDs are fully described in U.S. Pat. No. 4,985,459 to Sunshine et al., incorporated by reference herein in its entirety as to the description of such NSAIDs. Examples of useful NSAIDs include acetylsalicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen, bucloxic acid and mixtures thereof.

Also useful are the steroidal anti-inflammatory drugs such as hydrocortisone and the like, and COX-2 inhibitors such as meloxicam, celecoxib, rofecoxib, valdecoxib, etoricoxib or mixtures thereof. Mixtures of any of the above anti-inflammatories may be used.

Other materials that can be used as pharmaceutically active agent or pharmaceutically inactive precursor thereof include commonly known mouth and throat products. These products include, but are not limited to, upper respiratory agents such as phenylephrine, diphenhydramine, dextromethorphan, bromhexine and chlorpheniramine, gastrointestinal agents such as famotidine, loperamide and simethicone, anti-fungals such as miconazole nitrate, antibiotics and analgesics such as ketoprofen and fluributrofen.

The pharmaceutically active agent or pharmaceutically inactive precursor thereof may be also selected from sodium pyrosulphite, butylhydroxytoluene, butylated hydroxyanisole.

The pharmaceutically active agent or pharmaceutically inactive precursor thereof may be also selected from ephedrine, magaldrate, pseudoephedrine, sildenafil, xylocaine, benzalconium chloride, caffeine, phenylephrine, amfepramone, orlistat, sibutramine, acetaminophen, aspirin, glitazones, metformin, chlorpromazine, dimenhydrinat, domperidone, meclozine, metoclopramide, odansetron, prednisolone, promethazine, acrivastine, cetirizine, cinnarizine, clemastine, cyclizine, desloratadine, dexchlorpheniramine, dimenhydrinate, ebastine, fexofenadine, ibuprofen, levolevoproricin, loratadine, meclozine, mizolastine, promethazine, miconazole, chlorhexidine diacetate, fluoride, decapeptide KSL, aluminium fluoride, aminochelated calcium, ammonium fluoride, ammonium fluorosilicate, ammonium monofluorphosphate, calcium fluoride, calcium gluconate, calcium glycerophosphate, calcium lactate, calcium monofluorphosphate, calciumcarbonate, carbamide, cetyl pyridinium chloride, chlorhexidine, chlorhexidine digluconate, chlorhexidine chloride, chlorhexidine diacetate, CPP caseine phospho peptide, hexetedine, octadecentyl ammonium fluoride, potassium fluorosilicate, potassium chloride, potassium monofluorphosphate, sodium bi carbonate, sodium carbonate, sodium fluoride, sodium fluorosilicate, sodium monofluorphosphate, sodium tri polyphosphate, stannous fluoride, stearyl trihydroxyethyl propylenediamine dihydrofluoride, strontium chloride, tetra potassium pyrophosphate, tetrasodium pyrophosphate, tripotassium orthophosphate, trisodium orthophosphate, alginic acid, aluminium hydroxide, sodium bicarbonate, sildenafil, tadalafil, vardenafil, yohimbine, cimetidine, nizatidine, ranitidine, acetylsalicylic acid, clopidogrel, acetylcysteine, bromhexine, codeine, dextromethorphan, diphenhydramine, noscapine, phenylpropanolamine, vitamin D, simvastatin, bisacodyl, lactitol, lactulose, magnesium oxide, sodium picosulphate, senna glycosides, benzocaine, lidocaine, tetracaine, almotriptan, eletriptan, naratriptan, rizatriptan, sumatriptan, zolmitriptan, calcium, chromium, copper, iodine, magnesium, manganese, molybdenium, phosphor, selenium, zinc, chloramine, hydrogenperoxide, metronidazole, triamcinolonacetonide, benzethonium chl., cetyl pyrid. chl., chlorhexidine, fluoride, lidocaine, amphotericin, miconazole, nystatin, fish oil, Ginkgo biloba, ginseng, ginger, purple coneflower, saw palmetto, cetirizine, levocetirizine, loratadine, diclofenac, flurbiprofen, acrivastine pseudoephedrine, loratadine pseudoephedrine, glucosamine, hyaluronic acid, decapeptide KSL-W, decapeptide KSL, resveratrol, misoprostol, bupropion, ondansetron HCl, esomeprazole, lansoprazole, omeprazole, pantoprazole, rabeprazole, bacteria and the like, loperamide, simethicone, acetylsalicylic acid and others, sucralfate, clotrimazole, fluconazole, itraconazole, ketoconazole, terbinafine, allopurinol probenecid, atorvastatin, fluvastatin, lovastatin, nicotinic acid, pravastatin, rosuvastatin, simvastatin, pilocarpine, naproxen, alendronate, etidronate, raloxifene, risedronate, benzodiazepines, disulphiram, naltrexone, buprenorphine, codeine, dextropropoxyphene, fentanyl, hydromorphone, ketobemidone, ketoprofen, methadone, morphine, naproxen, nicomorphine, oxycodone, pethidine, tramadol, amoxicillin, ampicillin, azithromycin, ciprofloxacin, clarithromycin, doxycyclin, erythromycin, fusidic acid, lymecycline, metronidazole, moxifloxacin, ofloxacin, oxytetracycline, phenoxymethylpenicillin, rifamycins, roxithromycin, sulphamethizole, tetracycline, trimethoprim, vancomycin, acarbose, glibenclamide, gliclazide, glimepiride, glipizide, insulin, repaglinide, tolbutamide, oseltamivir, aciclovir, famciclovir, penciclovir, valganciclovir, amlopidine, diltiazem, felodipine, nifedipine, verapamil, finasteride, minoxidil, cocaine, buphrenorphin, clonidine, methadone, naltrexone, calcium antagonists, clonidine, ergotamine, β-blockers, aceclofenac, celecoxib, dexiprofen, etodolac, indometacin, ketoprofen, ketorolac, lornoxicam, meloxicam, nabumetone, oiroxicam, parecoxib, phenylbutazone, piroxicam, tiaprofenic acid, tolfenamic acid, aripiprazole, chlorpromazine, chlorprothixene, clozapine, flupentixol, fluphenazine, haloperidol, lithium carbonate, lithium citrate, melperone, penfluridol, periciazine, perphenazine, pimozide, pipamperone, prochlorperazine, risperidone, thioridizin, fluconazole, itraconazole, ketoconazole, voriconazole, opium, benzodiazepines, hydroxine, meprobamate, phenothiazine, aluminiumaminoacetate, esomeprazole, famotidine, magnesium oxide, nizatide, omeprazole, pantoprazole, fluconazole, itraconazole, ketoconazole, metronidazole, amphetamine, atenolol, bisoprolol fumarate, metoprolol, metropolol, pindolol, propranolol, auranofin, and bendazac.

Further examples of useful pharmaceutically active agents or pharmaceutically inactive precursors thereof can include active ingredients selected from the therapeutical groups comprising: Analgesic, Anaesthetic, Antipyretic, Anti-allergic, Anti-arrhythmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestant, Gastro-intestinal sedative, Sexual dysfunction agent, Disinfectants, Anti-diarrhoeal, Anti-anginal substance, Vasodilator, Anti-hypertensive agent, Vasoconstrictor, Migraine treating agent, Antibiotic, Tranquilizer, Antipsychotic, Anti-tumour drug, Anticoagulant, Antithrombotic agent, Hypnotic, Sedative, Anti-emetic, Anti-nauseant, Anticonvulsant, Neuromuscular agent, Hyper and hypoglycaemic, Thyroid and antithyroid, Diuretic, Antispasmodic, Uterine relaxant, Anti-obesity agent, Anorectic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretic, Anti-flatulent, Beta-blocker, Teeth Whitener, Enzyme, Co-enzyme, Protein, Energy booster, Fibre, Probiotics, Prebiotics, NSAID, Antitussives, Decongestants, Anti-histamines, Expectorants, Anti-diarrhoeals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful pharmaceutically active agents or pharmaceutically inactive precursors thereof may also include: Casein glyco-macro-peptide (CGMP), Triclosan, Cetyl pyridinium chloride, Domiphen bromide, Quaternary ammonium salts, zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniraminemaleate, Carbinoxamine maleate, Clemastine fumarate. Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbompheniamine, Guaifenesin, Ipecac, potassium iodide, Terpin hydrate, Loperamide, Famotidine, Ranitidine, Omeprazole, Lansoprazole, Aliphatic alcohols, Barbiturates, caffeine, strychnine, Picrotoxin, Pentyenetetrazol, Phenyhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, imipramine, Tranylcypromine, Phenelzine, Lithium, Sildenafil citrate, Tadalafil, and Vardenafil CL. For example, eugenol can be used as anaesthetic.

Examples of useful pharmaceutically active agent or pharmaceutically inactive precursor thereof may include active ingredients selected from the groups of ace-inhibitors, antianginal drugs, anti-arrhythmias, anti-asthmatics, anticholesterolemics, analgesics, anaesthetics, anticonvulsants, anti-depressants, anti-diabetic agents, anti-diarrhoea preparations, antidotes, anti-histamines, anti-hypertensive drugs, anti-inflammatory agents, anti-lipid agents, anti-manics, anti-nauseants, anti-stroke agents, anti-thyroid preparations, anti-tumour drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumour drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of useful pharmaceutically active agents or pharmaceutically inactive precursors thereof contemplated can also include antacids, H2-antagonists, and analgesics. For example, antacid dosages can be prepared using the ingredients calcium carbonate alone or in combination with magnesium hydroxide, and/or aluminium hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other useful pharmaceutically active agents or pharmaceutically inactive precursors thereof can include anti-diarrhoeals such as Immodium™ AD, anti-histamines, antitussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, antihistamines such as Claritin™, Hismanal™, Relafen™, and Tavist™; antiemetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™; and CaH-antagonists such as Procardia™, Adalat™, and Calan™.

The popular H2-antagonists which are contemplated for use in the present invention include cimetidine, ranitidine hydrochloride, famotidine, nizatidine, ebrotidine, mifentidine, roxatidine, pisatidine and aceroxatidine.

Active antacid ingredients can include, but are not limited to, the following: aluminium hydroxide, dihydroxyaluminium aminoacetate, aminoacetic acid, aluminium phosphate, dihydroxyaluminium sodium carbonate, bicarbonate, bismuth aluminate, bismuth carbonate, bismuth subcarbonate, bismuth subgallate, bismuth subnitrate, bismuth subsilysilate, calcium phosphate, citrate ion (acid or salt), amino acetic acid, hydrate magnesium aluminate sulphate, magaldrate, magnesium aluminosilicate, magnesium carbonate, magnesium glycinate, magnesium hydroxide, magnesium oxide, magnesium trisilicate, milk solids, aluminium mono-ordibasic calcium phosphate, tricalcium phosphate, potassium bicarbonate, sodium tartrate, sodium bicarbonate, magnesium aluminosilicates, tartaric acids and salts.

In some embodiments, the pharmaceutically active agent or pharmaceutically inactive precursor thereof can be selected from analgesics/anaesthetics such as menthol, phenol, hexylresorcinol, benzocaine, dyclonine hydrochloride, benzyl alcohol, salicyl alcohol, and combinations thereof. In some embodiments, the pharmaceutically active agent or pharmaceutically inactive precursor thereof can be selected from demulcents such as slippery elm bark, pectin, gelatin, and combinations thereof. In some embodiments, the pharmaceutically active agent or pharmaceutically inactive precursor thereof can be selected from antiseptic ingredients such as cetylpyridinium chloride, domiphen bromide, dequalinium chloride, eugenol and combinations thereof.

In some embodiments, the pharmaceutically active agent or pharmaceutically inactive precursor thereof can be selected from antitussive ingredients such as chlophedianol hydrochloride, codeine, codeine phosphate, codeine sulphate, dextromethorphan, dextromethorphan hydrobromide, diphenhydramine citrate, and diphenhydramine hydrochloride, and combinations thereof.

In some embodiments, the pharmaceutically active agent or pharmaceutically inactive precursor thereof can be selected from throat soothing agents such as honey, propolis, aloe vera, glycerine, menthol and combinations thereof. In still other embodiments, the pharmaceutically active agent or pharmaceutically inactive precursor thereof can be selected from cough suppressants. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants).

In still other embodiments, the pharmaceutically active agent or pharmaceutically inactive precursor thereof can be an antitussive selected from the group comprising codeine, dextromethorphan, dextrorphan, diphenhydramine, hydrocodone, noscapine, oxycodone, pentoxyverine and combinations thereof. In some embodiments, the pharmaceutically active agent or pharmaceutically inactive precursor thereof can be selected from antihistamines such as acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, the pharmaceutically active agent or pharmaceutically inactive precursor thereof can be selected from non-sedating antihistamines such as astemizole, cetirizine, ebastine, fexofenadine, loratidine, terfenadine, and combinations thereof.

For example, the one or more active ingredient(s) is/are selected from fragrances, flavours, essential oils, insecticide, fungicide, pharmaceutically active agent, or pharmaceutically inactive precursor thereof, e.g. antiseptic and/or anaesthetic, and mixtures thereof.

Method Step c)

In step c) of the method of the present invention, the surface-reacted calcium carbonate is saturated with the one or more active ingredient(s) in liquid form.

Before granulating the surface-reacted calcium carbonate particles, they are saturated with the one or more active ingredient(s).

Liquid saturation may be achieved by adding the one or more active ingredient(s) to dry or not completely saturated surface-reacted calcium carbonate.

According to the present invention, the particles are defined to be saturated, if the intraparticle pore volume of same is filled by the one or more active ingredient(s), and if present, the solvent in which the one or more active ingredient(s) is/are dissolved. For example, the particles are defined to be saturated, if the intraparticle pore volume of same is filled by at least 40 vol.-%, preferably at least 50 vol. %, based on the total intraparticle pore volume, with the one or more active ingredient(s), and if present, the solvent in which the one or more active ingredient(s) is/are dissolved.

Exceeding saturation may be seen visually by the onset of particles adhering one to another thus appearing to grow larger in size. Saturation of the material can be determined visually and tactually. In order to determine the optimal point, starting with the dry powder, the one or more active ingredient(s) might be added slowly by means of a spray bottle or some other means of evenly distributing the one or more active ingredient(s) into the powder. At the same time that the one or more active ingredient(s) is/are being added, or between each spray of the one or more active ingredient(s), it is important to mix the powder, Continual mixing of the powder will ensure that the one or more active ingredient(s) is/are properly distributed throughout. While this is occurring below saturation, the material will continue acting still like a powder, which means it flows unevenly, lightly and continues to dust when shaken. Occasional small clumps might still form, where the one or more active ingredient(s) level was added unevenly, but, prior to saturation, these are easily broken up again when worked back into the rest of the powder. For example, nearing, but not reaching saturation can be seen when the powder starts to feel cold to the hand, but still leaves the hand dry. If at this point, the material still looks powdery and does not appear to agglomerate, more of the one or more active ingredient(s) may be added. Saturation, or approximate saturation may be defined when the product no longer flows freely as a powder, instead appearing to agglomerate slightly and to stick together when pressed between the fingers.

Whereas, early in the method, when small agglomerates may be broken up easily by working them back into the rest of the powder and thus distributing the one or more active ingredient(s) throughout the material, upon reaching saturation, these agglomerates cannot be easily broken up, since the one or more active ingredient(s) is/are ubiquitous in the product and can therefore not be further distributed.

It is important that the material not be oversaturated wherein the material appears to form granules already or feels, looks or sticks like a mud. Thus, by these initial trials the necessary level of the active ingredient(s) can be determined, and subsequently, e.g. at a larger scale, other means of bringing the material to this solids level may be used, including automated mixing/active ingredient(s) addition or even drying a cake/slurry to the desired level.

The term "liquid" in the meaning of the present invention refers to a non-gaseous fluid composition, comprising or consisting of the one or more active ingredient(s), which is readily flowable at the pressure conditions and temperature of use, i.e. the temperature at which the method, preferably method step c), is carried out.

It is appreciated that method step c) can be carried out over a broad temperature and/or pressure range, provided that the one or more active ingredient(s) is in liquid form. For example, method step c) is carried out in a temperature range from 5 to 200° C., preferably from 10 to 120° C. and most preferably from 10 to 100° C. at ambient pressure conditions, i.e. at atmospheric pressure. Alternatively, method step c) is carried out in a temperature range from 5 to 200° C., preferably from 10 to 120° C. and most preferably from 10 to 100° C. at reduced pressure conditions, e.g. a pressure of from 100 to 700 mbar.

In one embodiment, method step c) is carried out at ambient temperature and pressure conditions, e.g., at room temperature, such as from about 5 to 35° C., preferably from 10 to 30° C. and most preferably from 15 to 25° C., and at atmospheric pressure. This embodiment preferably applies in case the one or more active ingredient(s) is/are liquid at room temperature or are dissolved in a solvent.

In case the one or more active ingredient(s) is/are dissolved in an organic solvent such as methanol, ethanol, n-butanol, isopropanol, n-propanol, acetone, dimethylsulphoxide, dimethylformamide, tetrahydrofurane, vegetable oils and the derivatives thereof, animal oils and the derivatives thereof, molten fats and waxes, and mixtures thereof, the organic solvent is preferably removed after method step c) e.g. by evaporation. In order to ensure a saturation of the surface-reacted calcium carbonate, the surface-reacted calcium carbonate is then preferably combined with water before method step d) is carried out.

If the one or more active ingredient(s) is/are solid at room temperature, such as from about 5 to 35° C., method step c) is carried out at a temperature such that the one or more active ingredient(s) is/are molten, e.g. from about 35 to 200° C., preferably from 45 to 120° C. and most preferably from 55 to 100° C., and at ambient pressure conditions, i.e. at atmospheric pressure, i.e. at atmospheric pressure, or at reduced pressure conditions, e.g. a pressure of from 100 to 700 mbar.

Method Step d)

In step d) of the method of the present invention, one or more binder is/are provided.

In one embodiment of the present invention, the one or more binder comprise(s), preferably consist(s) of, one binder. Alternatively, the one or more binder comprise(s), preferably consist(s) of, two or more binder. For example, the one or more binder comprise(s), preferably consist(s) of, two or three binder.

Preferably, the one or more binder comprise(s), preferably consist(s) of, one binder.

Binders which may be used in step d) of the present invention generally are those well-known in the art of granulation. In a preferred embodiment the one or more binder is selected from the group comprising synthetic polymers such as methylcellulose, ethylcellulose, sodium carboxymethylcellulose, hydroxypropyl methylcellulose (HPMC), hydroxypropylcellulose (HPC), ethylhydroxyethyl-cellulose (EHEC), polyvinyl pyrrolidone (PVP), polyethylene glycol (PEG), polyvinyl alcohols, polymethacrylates; and natural binders such as plant gums, e.g. acacia, tragacanth, sandarac, ghatti, karaya, locust bean and guar; proteins such as gelatin, casein, collagen; saccharides and polysaccharides such as starch and its derivatives, inulin, cellulose, pectins, carrageenans and sugars; animal exudates such as shellac; beeswax, alginic acid, and mixtures thereof.

In this respect, it is to be noted that, if required, the binder may also have disintegrating properties under certain conditions. Such binders, which are known in the art, e.g. physically modified starch, have binding properties under granulation conditions, but are able to disintegrate the granules by, e.g. moisture sorption and swelling, if required.

Typically, the one or more binder is added to the saturated surface-reacted calcium carbonate in an amount of from 0.1 to 50 wt.-%, preferably of from 0.2 to 25 wt.-%, more preferably of from 0.3 to 20 wt.-%, even more preferably of from 0.4 to 15 wt.-%, most preferably of from 0.5 to 10 wt.-%, e.g. 1 wt.-%, based on the total dry weight of surface-reacted calcium carbonate of step a).

Method Step e)

In step e) of the method of the present invention, the saturated surface-reacted calcium carbonate obtained in step c) is combined with the one or more binder of step d) under agitation in an agitation device.

The one or more binder may be added in dry form, or in the form of emulsions, dispersions, or solutions. In case where the binder is added in dry form or in a very high concentrated form, it may be possible that solvent is necessary during step e).

This solvent may generally be any one commonly used in the field of granulation, and is preferably selected from the group comprising water, methanol, ethanol, n-butanol, isopropanol, n-propanol, acetone and mixtures thereof. More preferably the solvent is water, ethanol and/or acetone. The most preferred solvent according to the present invention is water.

The selection of the solvent will depend on the nature of the binder in order to ensure an even distribution of same in the granulation method.

The solvent may contain minor amounts of compounds like minerals and salts such as those naturally occurring in the solvent, e.g. water. It may furthermore contain trace amounts of polymers commonly found in the water systems of production plants, such as for example surfactants, dispersing agents, flotation agents etc.

It is a preferred aspect of the present invention that less binder is needed according to the inventive method compared to a method where the surface-reacted calcium carbonate is saturated with the one or more binder before the addition of the one or more active ingredient(s).

As regards the order of addition, it is preferred that the one or more binder is added to the agitation device simultaneously with or after the saturated surface-reacted calcium carbonate obtained in step c).

It may, however, be necessary to adjust the amount of binder, the surface-reacted calcium carbonate and/or the saturated calcium carbonate, after the combination of the saturated surface-reacted calcium carbonate obtained in step c) and the one or more binder of step d) in step e).

Thus, it may be preferred that further surface-reacted calcium carbonate or saturated surface-reacted calcium carbonate or mixtures thereof, is added, if the mixture of step e) appears to be too liquid or paste-like.

Additional surface-reacted calcium carbonate or saturated surface-reacted calcium carbonate or mixtures thereof may be added in an amount of from 1 to 30 wt.-%, preferably of from 5 to 25 wt.-%, more preferably of from 8 to 20 wt.-%, based on the total dry weight of the surface-reacted calcium carbonate provided in step a).

On the other hand, if the mixture is too powder-like, it may be advantageous to add a solvent. When solvent addition is nearly sufficient, small agglomerates will form in a primary agglomerate phase, which might not have the desired size. Upon further addition of solvent, the granules will grow larger in size in what might be referred to as a secondary agglomeration phase, wherein the primary agglomerates then agglomerate to each other, and granules of a larger size may be obtained, if desired. This solvent may generally be any one commonly used in the field of granulation, and is preferably selected from the group comprising water, methanol, ethanol, n-butanol, isopropanol, n-propanol, acetone and mixtures thereof. More preferably the solvent is water, ethanol and/or acetone. The most preferred solvent is water.

The solvent may contain minor amounts of compounds like minerals and salts such as those naturally occurring in the solvent, e.g. water. It may furthermore contain trace amounts of polymers commonly found in the water systems of production plants, such as for example surfactants, dispersing agents, flotation agents, etc.

Thus, the method may further comprise a step f) of adding further surface-reacted calcium carbonate or saturated surface-reacted calcium carbonate or mixtures thereof, and/or solvent, preferably water, to the mixture obtained in step e) until an agglomeration of the particles is observed.

The addition of solvent may not be required, if the binder is added in the form of emulsions, dispersions, or solutions.

The mixture has the appropriate consistency as soon as the desired granule sizes, or granule size distribution, respectively, has been achieved, whereupon agitation may be continued.

The granulation equipment may be selected from the conventionally used ones for granulation purposes. Thus, the agitation device may be selected from the group comprising Eirich mixers, fluidized bed dryers/granulators, plate granulators, table granulators, drum granulators, disc granulators, dish granulators, ploughshare mixer, vertical or horizontal mixers, high or low shear mixer, high speed blenders and rapid mixer granulators.

It might be noted that there may be differences as regards the granule sizes or granule size distributions to be achieved depending on the method used or the speed of mixing.

For example, the use of a fluidized bed mixer for granulation appears to provide a more uniform granule size distribution than the Lödige mixer, whereas the Lödige mixer gives a wider size distribution. Thus, multiple size ranges may be provided.

In one embodiment, the method for the production of granules comprising surface-reacted calcium carbonate thus comprises, preferably consists of, the steps of
 a) providing surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
 b) providing one or more active ingredient(s) in liquid form,
 c) saturating the surface-reacted calcium carbonate with the one or more active ingredient(s) in liquid form,
 d) providing one or more binder,
 e) combining the saturated surface-reacted calcium carbonate obtained in step c) with the one or more binder of step d) under agitation in an agitation device, and
 f) adding further surface-reacted calcium carbonate or saturated surface-reacted calcium carbonate or mixtures thereof, and/or solvent, preferably water, to the mixture obtained in step e) until an agglomeration of the particles is observed.

In case a solvent is used in method step b), d), e) and/or f), it is preferred that the solvent is removed by means of separating the solvent from the resulting granules after the granulation step is completed, i.e. after step c) and/or e) and/or f), preferably after step e) or f.

In one embodiment, the method thus further comprise a step g) of removing the solvent from the mixture obtained in step c) and/or e) and/or f).

In case the one or more active ingredient(s) is/are dissolved in an organic solvent such as methanol, ethanol, n-butanol, isopropanol, n-propanol, acetone, dimethylsulphoxide, dimethylformamide, tetrahydrofurane, vegetable oils and the derivatives thereof, animal oils and the derivatives thereof, molten fats and waxes, and mixtures thereof, the organic solvent can be removed after method step c). In order to ensure a saturation of the surface-reacted calcium carbonate, the surface-reacted calcium carbonate is then preferably combined with water before method step d) is carried out.

The solvent is removed by means of separating the solvent from the resulting granules. This is preferably achieved by drying by means selected from the group comprising drying in a rotational oven, jet-drying, fluidized bed drying, freeze drying, flash drying and temperature-controlled high or low shear mixer.

In one embodiment, the method for the production of granules comprising surface-reacted calcium carbonate thus comprises, preferably consists of, the steps of
 a) providing surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source;
 b) providing one or more active ingredient(s) in liquid form,
 c) saturating the surface-reacted calcium carbonate with the one or more active ingredient(s) in liquid form,
 d) providing one or more binder,
 e) combining the saturated surface-reacted calcium carbonate obtained in step c) with the one or more binder of step d) under agitation in an agitation device,
 f) optionally adding further surface-reacted calcium carbonate or saturated surface-reacted calcium carbonate or mixtures thereof, and/or solvent, preferably water, to the mixture obtained in step e) until an agglomeration of the particles is observed, and
 g) removing solvent from the mixture obtained in step c) and/or e) and/or f).

The resulting granules may have a wide size range, wherein different size fractions may be separated by conventional means such as sieving.

Generally, the granules comprising surface-reacted calcium carbonate obtained after step e) and/or f) and/or g) have a volume median particle size of from 0.1 to 6 mm, preferably 0.2 to 5 mm and more preferably from 0.2 to 4 mm. Depending on the intended use of the granules size fractions of from 0.2 to 0.6 mm or 0.6 mm to 2 mm may be obtained, determined by sieve fractioning.

Additionally or alternatively, the granules comprising surface-reacted calcium carbonate obtained after step e) and/or f) and/or g) may have a specific surface area of from 10 to 180 $m^2/g$, preferably of from 15 to 150 $m^2/g$, more preferably of from 20 to 110 $m^2/g$, most preferably of from 30 to 70 $m^2/g$, measured using nitrogen and the BET method according to ISO 9277.

The granules obtained by the method according to the present invention have turned out to be more stable than those provided without binder or according to wet granulation without a previous saturation of the surface-reacted calcium carbonate. Furthermore, the granules are loaded with an active ingredient and thus can be used for a variety of applications.

Consequently, also the granules comprising surface-reacted calcium carbonate obtained by the method according to the present invention are an aspect of the present invention.

Another aspect of the present inventions refers to the use of the granules comprising surface-reacted calcium carbonate as fragrance delivery system, flavour delivery system, nutraceutical delivery system, pesticide delivery system, preservation delivery system, antioxidant delivery system, crop protection delivery system, fertilization delivery system, a scavenging system, a catalytic system, a shielding system for delicate molecules, a carrier system, a chemical delivery system or pharmaceutical delivery system, preferably a tablet, mini-tablet, capsule or pellet The following examples and tests will illustrate the present invention, but are not intended to limit the invention in any way.

EXAMPLES

1, Measurement Methods

Figure 1:
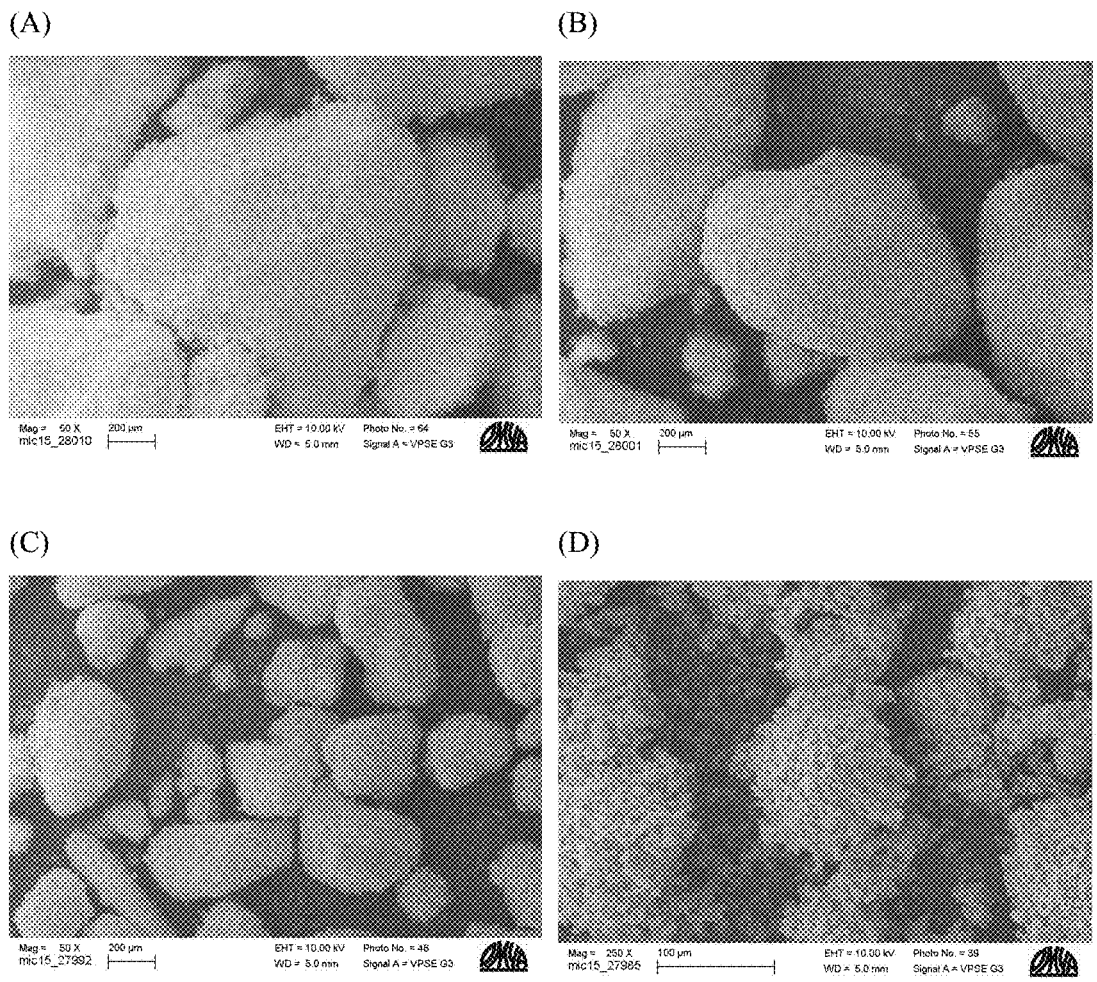
FIG. 1 shows SEM images of (E)-cinnamaldehyde loaded granules of different sieving fractions. A) 1-2 mm; B) 600 μm-1 mm; C) 300 μm-600 μm; D) <300 μm.

The following measurement methods were used to evaluate the parameters given in the examples and claims.

BET Specific Surface Area (SSA) of a Material

The BET specific surface area was measured via the BET process according to ISO 9277 using nitrogen, following conditioning of the sample by heating at 250° C. for a period of 30 minutes. Prior to such measurements, the sample was filtered, rinsed and dried at 110° C. in an oven for at least 12 hours.

Particle Size Distribution (Volume % Particles with a Diameter <X), $d_{50}$ Value (Volume Median Grain Diameter) and $d_{98}$ Value of a Particulate Material:

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement is analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 of Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

A vibrating sieve tower was used to analyze the particle size distribution of the granules. Aliquots of 120 g of granules were put on steel wire screen (Retsch, Germany) with mesh sizes of 300 µm, 600 µm, 1 mm and 2 mm. The sieving tower was shaken for 3 minutes with 10 seconds interval at a shaking displacement of 1 mm.

The processes and instruments are known to the skilled person and are commonly used to determine grain size of fillers and pigments.

Intra-Particle Intruded Specific Pore Volume (in $cm^3/g$)

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 µm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 µm down to about 1-4 µm showing the coarse packing of the sample between any agglomerate structures contributing strongly. Below these diameters lies the fine inter-particle packing of the particles themselves. If they also have intra-particle pores, then this region appears bi modal, and by taking the specific pore volume intruded by mercury into pores finer than the modal turning point, i.e. finer than the bi-modal point of inflection, we thus define the specific intra-particle pore volume. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the inter-particle pore region and the intra-particle pore region, if present. Knowing the intra-particle pore diameter range it is possible to subtract the remainder inter-particle and inter-agglomerate pore volume from the total pore volume to deliver the desired pore volume of the internal pores alone in terms of the pore volume per unit mass (specific pore volume). The same principle of subtraction, of course, applies for isolating any of the other pore size regions of interest.

2. Material and Equipment 2.1. Equipment

Lödige (Model L5, 51 Mixer)

2.2. Material

Surface-Reacted Calcium Carbonate

Surface-reacted calcium carbonate (SRCC) 1 ($d_{50}$=6.6 µm, $d_{98}$=13.7 µm, SSA=59.9 $m^2g^{-1}$) with an intra-particle intruded specific pore volume is 0.939 $cm^3/g$ (for the pore diameter range of 0.004 to 0.51 µm).

SRCC 1 was obtained by preparing 350 litres of an aqueous suspension of ground calcium carbonate in a mixing vessel by adjusting the solids content of a ground limestone calcium carbonate from Omya SAS, Orgon having a mass based median particle size of 1.3 µm, as determined by sedimentation, such that a solids content of 10 wt.-%, based on the total weight of the aqueous suspension, is obtained.

Whilst mixing the slurry at a speed of 6.2 m/s, 11.2 kg phosphoric acid was added in form of an aqueous solution containing 30 wt.-% phosphoric acid to said suspension over a period of 20 minutes at a temperature of 70° C. After the addition of the acid, the slurry was stirred for additional 5 minutes, before removing it from the vessel and drying using a jet-dryer.

Binder

Locust beam gum from *Ceratorin siliqua* seeds from Sigma-Aldrich (Galactomannan polysaccharide; G0753; CAS number 9000-40-2; EC number 232-541-5)

Pectin Citrus, Powder, CAS No. 9000-69-5, Alfa Aesar

Active: Ingredient (AI)

(E)-Cinnamaldehyde, ≥98%, FCC, FG, Sigma Aldrich, W228605, CAS No. 14371-10-9

Eugenol, ≥98%, FCC, FG, Sigma Aldrich, W246700, CAS No. 97-53-0, EC No. 202-589-1

Vanillin, FCC, CAS No. 121-33-5, Sigma Aldrich

3. Granulation Experiments

Lödige Mixer Granulation

Examples 1 and 2 (Inventive)

300 g surface-reacted calcium carbonate SRCC 1 was saturated with either (E)-cinnamaldehyde (Example 1) or eugenol (Example 2) and added to the Lödige mixer. Subsequently, 2.5 g Locust beam gum was added, dry, and the combination was mixed for several minutes to ensure proper blending. Subsequently, using a spray bottle, tap water was added over time, while mixing the powder with both the blending element (speed varied between 500 rpm and the maximum speed 850 rpm) and the cutter until the material started to look a little clumpy. The sample was mixed a few more minutes until individual granules were formed. The respective amounts from SRCC, active ingredient, binder and water, as well as the blending speed, can be taken from Table 1.

TABLE 1

| Example | SRCC [g] | Active Ingredient (AI) | Binder [g] | Binder type | Binder wt.-% on SRCC 1 | Blending speed [rpm] |
|---|---|---|---|---|---|---|
| 1 | 300 | (E)-cinnamaldehyde | 2.5 | Locust beam gum | 0.8% | 650-850 |
| 2 | 300 | eugenol | 2.5 | Locust beam gum | 0.8% | 650-850 |

Figure 2:
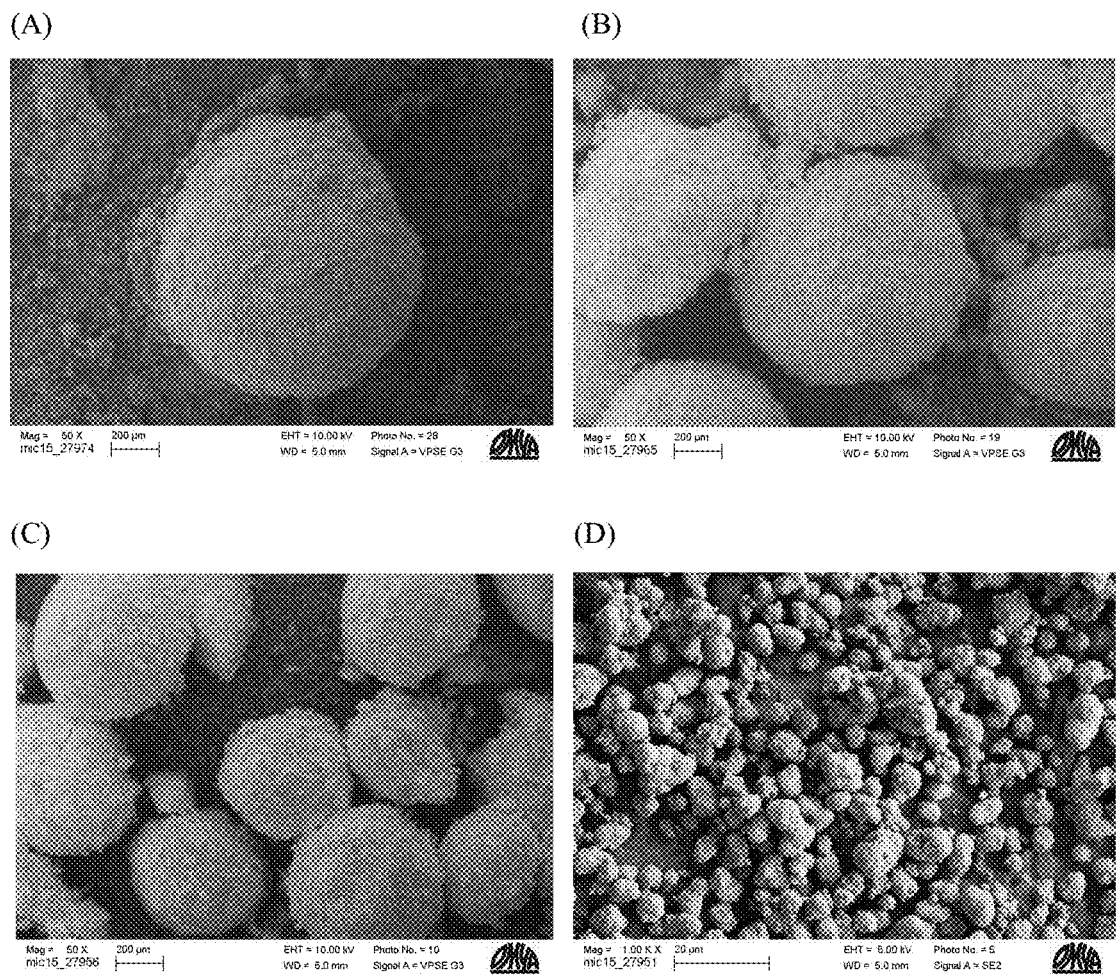
FIG. 2 shows SEM images of eugenol loaded granules of different sieving fractions. A) 1-2 mm; B) 600 µm-1 mm; C) 300 µm-600 µm; D) <300 µm.

A vibrating sieve tower was used to analyze the particle size distribution of the granules. The obtained granules were put on steel wire screens (Retsch, Germany) with mesh sizes of 300 µm, 600 µm, 1 mm and 2 mm. The sieving tower was shaken for 3 minutes with 10 seconds interval at a shaking displacement of 1 mm. The percentage of each fraction can be taken from Table 2. Example SEM images of the fractions can be observed in FIGS. 1 and 2.

TABLE 2

| | wt.-% of Particle size x [mm] | | | | |
|---|---|---|---|---|---|
| Example | x < 0.3 | 0.3 < x < 0.6 | 0.6 < x < 1 | 1 < x < 2 | x > 2 |
| 1 | 30.5 | 28.4 | 9.3 | 8.9 | 23.0 |
| 2 | 21.7 | 12.1 | 17.1 | 27.4 | 21.7 |

The above examples clearly show that granules can be produced from surface-reacted calcium carbonate being loaded with an active ingredient with standard binding agents.

Examples 3, 4, 5 and 6 (Inventive)

Loading

A. SRCC 1 Loaded with 30 wt.-% Vanillin 550 g surface-reacted calcium carbonate SRCC 1 was loaded by spraying while mixing in the Lödige mixer at 100 rpm with 786 g of a solution of vanillin in ethanol absolute (concentration=0.338 g/ml, 236 g vanillin in 550 g ethanol-abs.) to obtain surface-reacted calcium carbonate SRCC 1 loaded with 30 wt.-% vanillin (Examples 3 and 4). The remaining ethanol was evaporated by mixing at room temperature.

B. SRCC 1 Loaded with 10 wt.-% Vanillin 550 g surface-reacted calcium carbonate SRCC 1 was loaded by spraying while mixing in the Lödige mixer at 100 rpm with 336 g of a solution of vanillin in ethanol absolute (concentration=0.175 g/ml, 61 g vanillin in 275 g ethanol-abs.) to obtain surface-reacted calcium carbonate SRCC 1 loaded with 10 wt-% vanillin (Examples 5 and 6), The remaining ethanol was evaporated by mixing at room temperature.

Granulation 300 g of the respective vanillin loaded surface-reacted calcium carbonate SRCC 1 was used for each of the following granulation experiments.

Before adding the binder the surface-reacted calcium carbonate SRCC 1 loaded with 10 wt.-% vanillin (B) pores were saturated by spraying tap water on the mixing powder (ca. 60 g water). 2.5 g (Examples 3 and 5) or 6.0 g (Examples 4 and 6) Pectin Citrus were added, dry, to surface-reacted calcium carbonate SRCC 1 loaded with 30 wt.-% vanillin (A) or surface-reacted calcium carbonate SRCC 1 loaded with 10 wt.-% vanillin (B), and the combination was mixed for several minutes to ensure proper blending. Subsequently, using a spray bottle, tap water was added over time, while mixing the powder with both the blending element (speed varied between 500 rpm and the maximum speed 850 rpm) and the cutter until the material started to look a little clumpy. The sample was mixed a few more minutes until individual granules were formed. The granules were dried overnight at 60° C. The respective amounts from SRCC, active ingredient, binder and water, as well as the blending speed, can be taken from Table 3.

TABLE 3

| Example | SRCC [g] | Active Ingredient (AI) | Binder [g] | Amount of tap water used [g] | Binder type | Binder wt.-% on SRCC 1 | Blending speed [rpm] |
|---|---|---|---|---|---|---|---|
| 3 | 300 | vanillin (30 wt.-%) | 2.5 | 273.4 | Pectin Citrus | 0.8% | 500 |
| 4 | 300 | vanillin (30 wt.-%) | 6.0 | 253.4 | Pectin Citrus | 1.92% | 500 |
| 5 | 300 | vanillin (10 wt.-%) | 2.5 | 269.9 | Pectin Citrus | 0.8% | 500 |
| 6 | 300 | vanillin (10 wt.-%) | 6.0 | 276.0 | Pectin Citrus | 1.92% | 500 |

A vibrating sieve tower was used to analyze the particle size distribution of the granules. The obtained granules were put on steel wire screens (Retsch. Germany) with mesh sizes of 300 µm, 600 µm, 1 mm and 2 mm. The sieving tower was shaken for 3 minutes with 10 seconds interval at a shaking displacement of 1 mm. The percentage of each fraction can be taken from Table 4.

TABLE 4

| | wt.-% of Particle size x [mm] | | | | |
|---|---|---|---|---|---|
| Example | x < 0.3 | 0.3 < x < 0.6 | 0.6 < x < 1 | 1 < x < 2 | x > 2 |
| 3 | 4.1 | 5.7 | 12.7 | 55.4 | 22.1 |
| 4 | 3.9 | 10.4 | 22.2 | 48.6 | 14.9 |
| 5 | 0.7 | 0.2 | 0.2 | 1.0 | 97.9 |
| 6 | 4.1 | 30.1 | 22.1 | 27.3 | 16.4 |

The above examples clearly show that granules can be produced from surface-reacted calcium carbonate being loaded with an active ingredient with standard binding agents.

The invention claimed is:

1. A method for the production of granules comprising surface-reacted calcium carbonate, the method comprising:
   a) providing surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source,
   b) providing one or more active ingredient(s) in liquid form,
   c) saturating the surface-reacted calcium carbonate with the one or more active ingredient(s) in liquid form,
   d) providing one or more binder, and
   e) combining the saturated surface-reacted calcium carbonate obtained in step c) with the one or more binder of step d) under agitation in an agitation device, and
   wherein the granules comprising surface-reacted calcium carbonate obtained after step e) have a volume median particle size of from 0.1 to 6 mm determined by sieve fractioning.

2. The method according to claim 1, wherein the natural ground calcium carbonate is selected from calcium carbonate containing minerals selected from the group comprising marble, chalk, dolomite, limestone and mixtures thereof; and that the precipitated calcium carbonate is selected from the group comprising precipitated calcium carbonates having aragonitic, vateritic or calcitic mineralogical crystal forms or mixtures thereof.

3. The method according to claim 1, wherein the surface-reacted calcium carbonate has
   i) a specific surface area of from 15 m$^2$/g to 200 m$^2$/g, measured using nitrogen and the BET method according to ISO 9277, and/or
   ii) a volume median grain diameter $d_{50}$ of from 1 to 75 µm, and/or
   iii) an intra-particle intruded specific pore volume in the range from 0.1 to 2.3 cm$^3$/g, calculated from mercury porosimetry measurement, and/or
   iv) a grain diameter $d_{98}$ (vol) of from 2 to 150 µm.

4. The method according to claim 1, wherein in step b), the one or more active ingredient(s) is/are dissolved in a solvent selected from the group consisting of water, methanol, ethanol, n-butanol, isopropanol, n-propanol, acetone, dimethylsulphoxide, dimethylformamide, tetrahydro furane, vegetable oils and derivatives thereof, animal oils and the derivatives thereof, molten fats and waxes, and mixtures thereof.

5. The method according to claim 1, wherein in step b), the one or more active ingredient(s) is/are selected from the group consisting of fragrances, flavours, herbal extracts, fruit extracts, nutrients, trace minerals, repellents, food, cosmetics, sweeteners, flame retardants, enzymes, pesticides, fertilizers, preserving agents, antioxidants, reactive chemicals, pharmaceutically active agents or pharmaceutically inactive precursors thereof, and mixtures thereof.

6. The method according to claim 1, wherein the one or more binder of step d) is selected from the group consisting of synthetic polymers and natural binders and mixtures thereof.

7. The method according to claim 1, wherein the one or more binder of step d) is added in an amount of from 0.1 to 50 wt.-%, based on the total dry weight of surface-reacted calcium carbonate of step a).

8. The method according to claim 1, wherein in step e), the agitation device is selected from the group consisting of Eirich mixers, fluidized bed dryers/granulators, plate granulators, table granulators, drum granulators, disc granulators, dish granulators, ploughshare mixer, vertical or horizontal mixers, high or low shear mixer, high speed blenders and rapid mixer granulators.

9. The method according to claim 1, wherein in step e), the one or more binder is added to the agitation device simultaneously with or after the saturated surface-reacted calcium carbonate obtained in step c).

10. The method according to claim 1, wherein the method further comprises a step f) of adding further surface-reacted calcium carbonate or saturated surface-reacted calcium carbonate or mixtures thereof, and/or solvent, to the mixture obtained in step e) until an agglomeration of the particles is observed.

11. The method according to claim 10, wherein the further surface-reacted calcium carbonate or saturated surface-reacted calcium carbonate or mixtures thereof is added in an amount of from 1 to 30 wt, based on the total dry weight of the surface-reacted calcium carbonate provided in step a).

12. The method according to claim 10, wherein the method further comprises a step g) of removing the solvent from the mixture obtained in step c) and/or e) and/or f).

13. The method according to claim 12, wherein in step g), the solvent is removed by means of separating the solvent from the resulting granules.

14. The method according to claim 1, wherein the granules comprising surface-reacted calcium carbonate obtained after step e) have a specific surface area of from 10 to 180 m$^2$/g, measured using nitrogen and the BET method according to ISO 9277.

15. Granules comprising surface-reacted calcium carbonate formed by the method according to claim 1.

16. A fragrance delivery system, flavour delivery system, nutraceutical delivery system, pesticide delivery system, preservation delivery system, antioxidant delivery system, crop protection delivery system, fertilization delivery system, a catalytic system, a shielding system for delicate molecules, a carrier system, a chemical delivery system or pharmaceutical delivery system comprising the granules of claim 15.

17. The method according to claim 10, wherein the granules comprising surface-reacted calcium carbonate obtained after steps e) and f) or step f) alone have a volume median particle size of from 0.1 to 6 mm, determined by sieve fractioning.

18. The method according to claim 12, wherein the granules comprising surface-reacted calcium carbonate obtained after steps e), f) and g) or steps e) and f) or steps f) and g) or step f) alone or step g) alone have a volume median particle size of from 0.1 to 6 mm, determined by sieve fractioning.

19. The method according to claim 1, wherein the granules comprising surface-reacted calcium carbonate obtained after step e) have a volume median particle size of from 0.2 to 4 mm, determined by sieve fractioning.

20. The method according to claim 1, wherein the granules comprising surface-reacted calcium carbonate obtained after step e) have a volume median particle size of from 0.2 to 0.6 mm, determined by sieve fractioning.

21. The method according to claim 1, wherein the granules comprising surface-reacted calcium carbonate obtained after step e) have a volume median particle size of from 0.6 to 2 mm, determined by sieve fractioning.

* * * * *